United States Patent [19]
Pruthi et al.

[11] Patent Number: 6,106,839
[45] Date of Patent: Aug. 22, 2000

[54] AYURVEDIC COMPOSITION FOR THE TREATMENT OF DISORDERS OF THE NERVOUS SYSTEM INCLUDING PARKINSON'S DISEASE

[76] Inventors: Som C. Pruthi; Puneet Pruthy, both of 2001 N. Ocean Blvd., #1602, Boca Raton, Fla. 33431

[21] Appl. No.: 09/321,917

[22] Filed: May 29, 1999

[51] Int. Cl.[7] ............................ A01N 65/00; A61F 13/00; A61K 9/48; A61K 9/20
[52] U.S. Cl. ........................ 424/195.1; 424/422; 424/451; 424/464; 424/465
[58] Field of Search ................................ 424/195.1, 422, 424/451, 464, 465

[56] References Cited

PUBLICATIONS

Pras et al.; *Mucuna pruriens*: improvement of the biotechnological production of the anti–Parkinson drug L–dopa by plant cell selection; Pharm Word Sci; 15(6);263–8, Dec. 1993.

Houghton et al.; The effect of blood clotting of some west African plants used against snakebite; J Ethnopharmacol; 44(2):99–108, Oct. 1994.

*Primary Examiner*—Thurman K. Page
*Assistant Examiner*—Susan Tran
*Attorney, Agent, or Firm*—Robert M. Downey, P.A.

[57] ABSTRACT

A composition for use in treating nervous disorders, including Parkinson's disease, includes: *Mucuna Pruriens,* in an amount of between 55% and 99% by weight of the composition; *Piper Longum,* in an amount of between 10% and 35% by weight of the composition; and *Zingiber Officinalis,* in an amount of between 5% and 15% by weight of the composition.

6 Claims, No Drawings

AYURVEDIC COMPOSITION FOR THE TREATMENT OF DISORDERS OF THE NERVOUS SYSTEM INCLUDING PARKINSON'S DISEASE

BACKGROUND OF THE INVENTION

1. Field of the Invention

The present invention relates to an Ayurvedic composition, and more particularly, to a composition comprising natural ingredients for the treatment of disorders of the nervous system including Parkinson's disease.

2. Description of the Related Art

Parkinson's disease (PD) is a chronic illness which is affecting an increasing percentage of the world's population over the age of 40. In the United States alone, there are over 1 million patients who presently suffer from the symptoms of Parkinson's disease. Individuals developing this dreaded degenerative disease face many debilitating physical, psychological and social changes.

Primary symptoms of Parkinson's disease:

| | |
|---|---|
| Rigidity: | muscle stiffness |
| Tremors: | may start in one side of the body, in the arms and later in the legs |
| Bradykinesia: | restriction of movement, difficulty in walking |

Secondary symptoms of Parkinson's disease include:

Depression

Sleep disturbance

Senility, difficulty with memory

Slurring, speech problem

Drooling, difficulty to swallow saliva

Stooped posture

Parkinson's disease may start with tremors in one or both hands which may eventually lead to the arms and legs. Rigidity and difficulty in holding objects and maintaining balance can lead to impaired movements and dependency on others to perform even the simplest of daily tasks.

At present, there is no known cure for Parkinson's disease. There are a variety of drugs which are available to treat the symptoms of Parkinson's disease, including: levedopa, carbidopa, Amantadine, Anticholinergic, and Dopamine Agonists. Most of these drugs, if not all of them, have serious side effects. Further, these drugs do not provide a cure nor do they slow the progression of Parkinson's disease. After prolonged use of any of these drugs, there effectiveness in treating the symptoms of Parkinson's disease becomes less effective. At present, the only treatment available involves experimenting with these and other drugs to determine how each individual patient can tolerate the specific drugs without serious side effects. Eventually, a patient's drugs will have to be changed as previously administered drugs become ineffective.

Most of the people with Parkinson's disease suffer a gradual health decline due to a weakened nervous system. This gradual decline in health eventually leads to a severe disability. The drugs and patient care for the treatment of Parkinson's disease are costly and are needed for over a prolonged period of time, as the patient suffers a long, gradual decline in health.

Accordingly, there is an urgent need for an effective, less expensive means of treating Parkinson's disease, as well as other disorders of the nervous system, without the patient suffering from side effects. The present invention addresses this compelling need and provides a composition of natural herbal ingredients for treating nervous disorders, including Parkinson's disease, without toxicity and negative side effects.

SUMMARY OF THE INVENTION

The present invention is directed to a composition for the treatment of disorders of the nervous system including Parkinson's disease. The composition has been shown to slow the progression of Parkinson's symptoms (e.g., tremors, rigidity, slurring, drooling, balance, etc.). The composition comprises three natural herbal ingredients including *Mucuna Pruriens* seeds, *Piper Longum* fruit and roots of *Zingiber Officinalis*. In a preferred embodiment, the composition is manufactured in the form of powder. The composition may also be manufactured as capsules, tablets, syrup or in a liquid form for subcutaneous injection.

DETAILED DESCRIPTION OF THE PREFERRED EMBODIMENT

The composition includes the combination of: Cow-hage, botanical name *Mucuna Pruriens*, in an amount of between 55% and 99% by weight; Long-Papper, botanical name *Piper Longum*, in an amount of between 10% and 35% by weight; and Ginger, botanical name *Zingiber Officinalis*, in an amount of between 5% and 15% by weight.

Cow-hage is an annual climbing shrub with golden brown legumes that are cooked and eaten in the tropics. Its seeds, roots and legumes are known to have medicinal value in Ayurvedic practice. Long-Papper is a plant indigenous to India and Shri Lanka. Its berries are known to have medicinal values. Ginger is used all over the world as a spice in cooking and is known to have therapeutic values for digestive disorders and many other benefits.

The composition of the present invention is prepared by soaking seeds (or roots, legumes) from Cow-hage in water or milk overnight. The seed coverings and other impurities are removed and dried slowly. After drying, grinding is done in stages to fine powder. Excessive grinding must be avoided to prevent overheating and destroying of the natural properties of the herb. Therefore, it is best to grind in a series of steps, wherein smaller particles are separated from a remainder of the particles by screening. Thereafter, the smaller particles of a predetermined maximum size are further ground and again separated, repeating this process in a series of steps to produce a fine powder. In a preferred embodiment, the process of grinding is accomplished with the use of a mortar and pestle. A series of sieves, each having predetermined size opening in the screen, are used to separate the ground herb throughout the grinding process. Dried berries of Long-Papper are used to make a fine powder in steps as above. Aged Long-Pappers are preferred. Here, also, excessive heating during grinding must be avoided by grinding in a series of steps as described above. Dried ginger roots are similarly ground to fine powder in many steps.

All three powders (*Mucuna Pruriens*, *Piper Longum*, *Zingiber Officinalis*) are placed in a mixing chamber in accordance with their specified percentage by weight. The three powders are mixed at slow speed, by stirring, until a homogenous blend is achieved. The homogenous powder mixture is then kept in a cool, dry place until use. The powder mixture can be administered directly to the patient or used in the manufacture of tablets, syrups or other forms in accordance with the manufacturing techniques which are well known in the field.

The powder, incorporating the composition of the present invention, is preferably administered to the Parkinson's patient (in powder form, capsules, tables or syrup) in a concentration between 2 to 6 grams per day. To treat Parkinson's, the composition should be administered in dosages of 1 to 1.5 grams with lukewarm milk or water taken 2 to 4 times a day, at equally divided intervals during the day.

Improvement will ordinarily be observed in 60 to 90 days from the beginning of the treatment, depending on the existing condition. During the treatment period, consumption of spices, alcohol, and meat must be avoided. Smoking should also be avoided. Physician prescribed medication and therapy should not be interrupted.

In order to verify the effectiveness of the composition of the present invention in treating Parkinson's disease, a 12 year study was performed. The study was conducted under the supervision of a physician, the results of which are set forth below.

Patient Testing
    Female
    62 years of age
    Term of disease: diagnosed with PD in August 1986
    Comments: Tried available treatment; had severe side effects
    Date treatment started: February 20, 1988
    Date treatment stopped: Ongoing treatment
    Side effects: None

| PD symptoms | Beginning of Treatment February, 1988 | 11 years after treatment March, 1999 |
| --- | --- | --- |
| Tremors | Yes (left hand) | Yes (slightly more) |
| Rigidity | No | Some |
| Balance/walking | No difficulty | Some difficulty |

Comments
1. Very slow progression of Parkinson's disease over 11 year period (age 51 through 62).
2. Patient still functional, can perform most daily routines without any assistance (PD specialists surprised and extremely impressed with patient's progression).

What is claimed is:

1. A composition for the treatment of Parkinson's disease, the composition comprising the following ingredients:

*Mucuna Pruriens,* in an amount of between 55% and 99% by weight of the composition;

*Piper Longum,* in an amount of between 10% and 35% by weight of the composition; and

*Zingiber Officinalis,* in an amount of between 5% and 15% by weight of the composition.

2. A composition for the treatment of Parkinson's disease, the composition comprising the following ingredients:

powder of *Mucuna Pruriens* derived from seeds, roots, and legumes in an amount of between 55% and 99% by weight of the composition;

powder of *Piper Longum,* derived from dried berries, in an amount of between 10% and 35% by weight of the composition; and powder of *Zingiber Officinalis,* derived from dried ginger roots, in an amount of between 5% and 15% by weight of the composition.

3. The composition as recited in claim 2 wherein said composition is contained in a capsule form comprising 1 gram to 1.5 grams of said composition.

4. The composition as recited in claim 2 wherein said composition is contained in a tablet form comprising 1 gram to 1.5 grams of said composition.

5. The composition as recited in claim 2 wherein said composition is contained in a syrup form for oral consumption in an amount of between 1 gram and 1.5 grams of said composition.

6. The composition as recited in claim 2 wherein said composition is contained in a liquid form for subcutaneous injection, wherein the composition is administered in dosages of between 1 gram and 1.5 grams.

\* \* \* \* \*